United States Patent [19]
Okada et al.

[11] Patent Number: 6,166,656
[45] Date of Patent: Dec. 26, 2000

[54] EMERGENCY ASSISTANCE SYSTEM FOR AUTOMOBILE ACCIDENTS

[75] Inventors: Tsuyoshi Okada; Takumi Ajima, both of Kanagawa, Japan

[73] Assignee: Matsushita Electric Industrial Co., Ltd., Osaka, Japan

[21] Appl. No.: 09/401,001

[22] Filed: Sep. 21, 1999

[30] Foreign Application Priority Data

Sep. 21, 1998 [JP] Japan ................... 10-283610

[51] Int. Cl.[7] ................................................. G08G 1/00
[52] U.S. Cl. ................. 340/901; 340/573.1; 340/825.36; 342/457
[58] Field of Search ................. 340/539, 573.1, 340/471, 425.5, 426, 825.36, 825.49; 379/37, 38; 342/457

[56] References Cited

U.S. PATENT DOCUMENTS

| | | | |
|---|---|---|---|
| 3,823,384 | 7/1974 | Messmer et al. | 340/84 |
| 4,717,904 | 1/1988 | Murakami | 340/52 H |
| 5,223,844 | 6/1993 | Mansell et al. | 342/357 |
| 5,334,974 | 8/1994 | Simms et al. | 340/990 |
| 5,515,285 | 5/1996 | Garrett, Sr. et al. | 364/460 |
| 5,570,087 | 10/1996 | Lemelson | 340/870.05 |
| 5,576,952 | 11/1996 | Stutman et al. | 364/413.02 |
| 5,757,284 | 5/1998 | Trizzino et al. | 340/902 |
| 5,808,564 | 9/1998 | Simms et al. | 340/990 |
| 5,960,337 | 9/1999 | Brewster et al. | 455/404 |

FOREIGN PATENT DOCUMENTS

| | | |
|---|---|---|
| 06-028590 | 2/1994 | Japan . |
| 08-124069 | 5/1996 | Japan . |
| 09-198592 | 7/1997 | Japan . |

*Primary Examiner*—Daniel J. Wu
*Assistant Examiner*—Phung Nguyen
*Attorney, Agent, or Firm*—Ratner & Prestia

[57] ABSTRACT

An emergency assistance system for summoning first-aid assistance of persons and vehicles within the vicinity of a person involved in an automobile accident, while also making an emergency call to rescue and police authorities. An accident alarm is provided for announcing the occurrence of an accident to vehicles and persons in the vicinity of an accident in order to seek their help and to prevent a secondary disaster. In addition, first-aid equipment is provided to give first-aid treatment, for example, to maintain body temperature and restoration consciousness to prolong life of an injured person. In a automobile accident, an emergency measure is taken by the emergency equipment provided in the accident vehicle, such as notification of the occurrence of the accident and the need for medical assistance.

19 Claims, 6 Drawing Sheets

FIG. 3A  Hazard lamp flashing

FIG. 3B  Normal car stop

FIG. 3C  Emergency

FIG. 4A  Hazard lamp ON

FIG. 4B  Brake lamp ON

EMERGENCY ASSISTANCE SYSTEM FOR AUTOMOBILE ACCIDENTS

FIELD OF THE INVENTION

The present invention relates to the field of emergency assistance system (hereinafter referred as emergency equipment) for automobile accidents, and more particularly to emergency equipment for saving the lives of drivers or the passengers (hereinafter referred as persons) and minimizing injury after the occurrence of accidents such as collisions.

BACKGROUND OF THE INVENTION

A number of convent ional invention s related too emergency equipment for use in the case of automobile accidents are disclosed, including Japanese Laid-open Patents Nos. H9-198592, H6-28590, and H8-124069.

Figure 8:
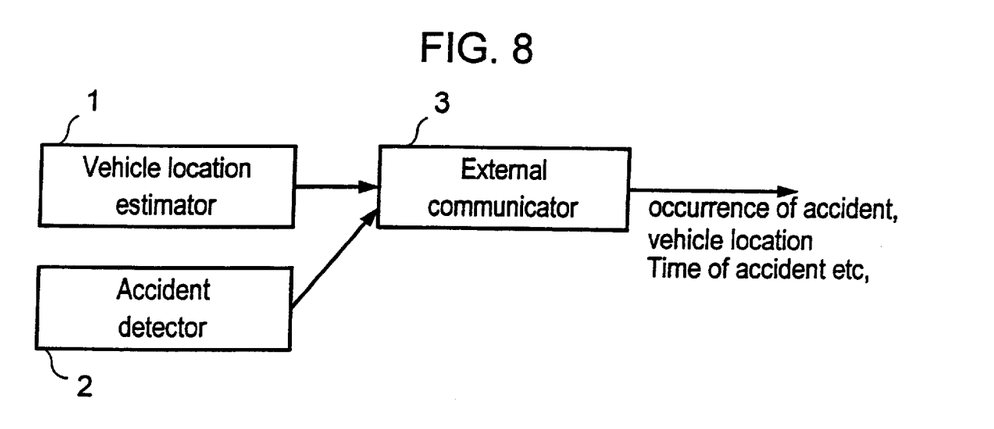
FIG. 8 is a block diagram of emergency equipment for use in the case of automobile accidents of the prior art.

An emergency equipment of the prior art for use in the case of automobile accidents is described next with reference to a drawing. FIG. 8 is a block diagram of the conventional emergency equipment for use in the case of automobile accidents. In FIG. 8, a vehicle location estimator 1 identifies the direction by integrating a gyro output, and its accumulated distance by integrating the output of the vehicle velocity pulse, while correcting its absolute position using a GPS (Global Positioning System), for example. The GPS identifies an absolute signal receiving position based on information transmitted from satellites. The present position of the vehicle is then calculated by finding the travel trajectory based on the direction and accumulated distance information. The vehicle's actual position may be more accurately identified by collating the current vehicle position or trajectory with map data stored typically on a CD-ROM or DVD.

An accident detector 2 is a device for recognizing whether an accident has occurred by means of either manual operation or detection of specific abnormalities in the car using an onboard sensor. For manual operation, one example is to provide a button for initiating the accident detector 2 near the driver's or the passenger's seat. The occurrence of an accident may also be detected by providing an acceleration sensor for detecting an impact of collision or a roll sensor for detecting overturning (by detecting the rolling of a small object inside, or using a gyroscope), and detecting any change in its output.

An external communicator 3 transmits information to prescribed addresses typically using a modem and mobile phone when the accident detector 2 detects the accident. Information communicated may include the vehicle owner, accident time, and the present position identified by the vehicle location estimator 1. Probable prescribed addresses may include a district police station or fire station for notifying the occurrence of an accident, and a rescue association if there is any damage to the vehicle.

Using the above configuration, any abnormalities such as accidents are promptly notified to prescribed addresses so that emergency situations such as vehicle breakdown or injury of the passengers due to an automobile accident can be promptly informed to the relevant external organizations.

With the above configuration of conventional emergency equipment for use in the case of automobile accidents, however, insufficient measures are provided with respect to the rescue or prolongation of the life of the persons in the vehicle, since the conventional equipment merely transmits information to the prescribed addresses.

In many automobile accidents, life is in danger even while the emergency is being reported. It may be further necessary to ask for help from nearby persons by publicly announcing the occurrence of an accident as soon as possible, or to apply first-aid treatment to prolong life until the rescue squad arrives.

SUMMARY OF THE INVENTION

The present invention is for providing an injured person with first-aid or life-prolonging treatment and prolong life by detecting the degree of injury.

The emergency equipment of the present invention is for use in automobile accidents and includes an accident alarm to alert persons and vehicles in the vicinity of an accident site. With this configuration, nearby vehicles and persons are notified of the occurrence of the accident and an injured person can receive immediate attention and ask for help.

The present invention is also equipped with an person injury detector for detecting the degree of injury and a first-aid equipment for giving an injured person first-aid and life-prolonging treatment based on the results of the person injury detector. This configuration enables to detect the degree of injury of the person, and give the person first-aid and life prolonging treatment.

As described above, the emergency equipment for use in the case of automobile accidents of the present invention comprises the vehicle location estimator for estimating a vehicle position, accident detector for detecting the accident by person's manual operation or onboard sensor, external communicator for informing of the accident and the driver's health condition to emergency response organizations such as a police station and fire station, and an accident alarm for the surrounding area to announce to the surrounding vehicles and pedestrians that an accident has occurred so as to get their attention and ask for help. This configuration enables the notification to prescribed addresses and the calling of the immediate attention of vehicles and pedestrians near the accident site. A victim of the accident may also be rescued promptly.

Since the present invention is equipped with the person injury detector for detecting the degree of injury of the person and the first-aid equipment for applying first-aid or life-prolonging treatment to the person based on information from the person injury detector, active life-prolonging measures may be applied after confirming the injury suffered by the person. This enables the increasing of the survival rate of any injured persons.

The accident alarm for the surrounding area is configured to flash the hazard lamps in a faster cycle than normal car parking based on driver's instruction so that the surrounding vehicles and pedestrians are notified immediately of an emergency situation due to an accident. This enables to notify surrounding people immediately of a vehicle in a trouble due to an accident or other problems.

The accident alarm for the surrounding area further turns on the hazard lamps and brake lamps alternately or the hazard lamps and head lamps alternately so that the surrounding vehicles and pedestrians are notified immediately of an emergency situation due to an accident. This enables to notify surrounding people immediately of a vehicle in a trouble due to an accident or other problems.

The accident alarm for the surrounding area further turns on the hazard lamps or brake lamps mounted on both sides of the car alternately, such as right lamp, left lamp, and then right lamp again; so that the surrounding vehicles and pedestrians are notified immediately of an emergency situation due to accident. This enables to notify surrounding people immediately of a vehicle in a trouble due to an accident or other problems.

The accident alarm for the surrounding area is further a small broadcasting equipment for locally transmitting information to notify unspecified third party nearby of accident information including an accident site location and accident occurrence time, so that the surrounding vehicles and pedestrians are notified immediately of an emergency situation due to accident. This enables the informing of surrounding vehicles and residents who cannot directly look at the site of the accident or any problem, and catch their attention to ask for help.

The person injury detector in the present invention has a detector embedded in the person's seat for measuring the person's body temperature, blood pressure, or pulse, and recognizing the person's condition from changes in body temperature, blood pressure, or pulse. This makes it possible to obtain a range of data related to the person's condition simply by having the person contacting the seat without requiring any specific operation of the person.

The first-aid equipment turns on the heater embedded under the person's seat to suppress drop in body temperature as much as possible in response to recognition of injury to the person based on drop in body temperature, blood pressure, or pulse detected by the person injury detector. This delay weakening caused by lowering body temperature of the injured person in danger of death, and prolongs life by maintaining physical strength as much as possible.

The first-aid equipment further tries to bring back the weakening person, due to fainting, to full consciousness by means of voice encouragement or a blinking light in response to the recognition of damage to the person based on drop in body temperature, blood pressure, or pulse. This enables to restore full consciousness of the injured person in danger of death, and encourage the person as much as possible to prolong life.

The first-aid equipment further explains the first-aid procedures to the person by voice and images. This calms down the person even if a person is in a state of panic due to the sudden accident and resultant injury, allowing first-aid treatment to be promptly self-administered.

The first-aid equipment still further detects the condition of the damaged car and surrounding area to give instructions for refuge, guidance, and emergency measures as well as information on the condition of the person to allow a person to be given first-aid treatment. This enables to give first-aid in a broader sense including refuge and emergency measures.

The first-aid equipment still further determines whether the car is on ordinary road or freeway based on information from the car navigation system, and informs the person suitable for each type of road. This enables the application of more appropriate emergency instructions in accordance with the characteristics of each type of road and the degree of danger.

The person injury detector is further equipped with a conversation equipment or interactive information input device in order to obtain information directly from the person as well as that from the person injury detector. The first-aid equipment can give appropriate first-aid instructions to the person based on the injury recognition result of the person injury detector. By obtaining information directly from the persons after calming them if they are upset due to the sudden accident, or by making the persons treat themselves, appropriate first-aid treatment may be given promptly.

The accident alarm for the surrounding area further automatically honks the horn intermittently for long time so that surrounding vehicles and pedestrians are immediately informed of an emergency situation due to an accident. This enables to notify the surrounding people of the car in the accident or in trouble by hearing continuous horn sound and changes which normally does not happen.

The accident alarm for the surrounding area further automatically sounds the horn when receiving signals from the emergency vehicle such as an ambulance. This enables emergency vehicles such as an ambulance to find the car involved sooner, reducing the time taken for rescue.

DESCRIPTION OF THE PREFERRED EMBODIMENT

Exemplary embodiments of the present invention are described below in detail with reference to FIGS. 1 to 7.

First exemplary embodiment

Figure 1:
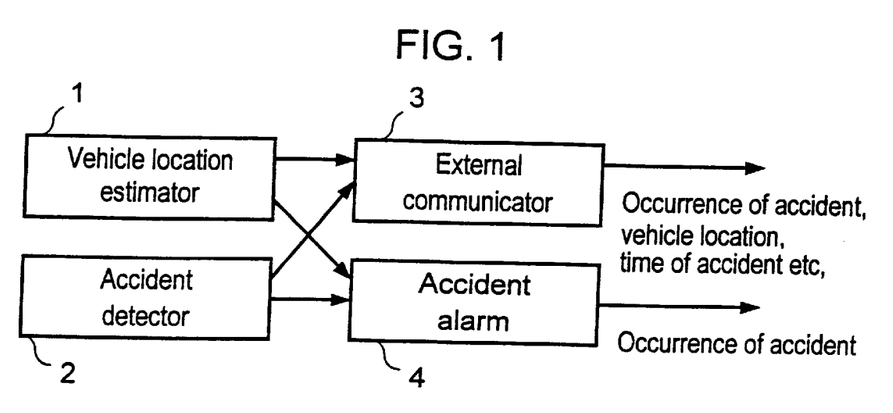
FIG. 1 is a block diagram of emergency equipment for use in the case of automobile accidents in accordance with a first exemplary embodiment in the present invention.

FIG. 1 is a block diagram of an emergency equipment for use in the case of automobile accidents in accordance with a first exemplary embodiment of the present invention. The emergency equipment in the first exemplary embodiment, as shown in FIG. 1, comprises a vehicle location estimator 1 based on a location system such as GPS, an accident detector 2 such as an acceleration sensor, an external communicator 3 such as a mobile phone, and an accident alarm for the surrounding area 4. Since the operation of the vehicle location estimator 1, accident detector 2, and external communicator 3 are the same as that of the prior art, their description is omitted here.

In the case of automobile accidents, a person may be injured and in danger of death. In such a situation, it is necessary to call immediately for rescue to the maximum extent possible, including the surrounding area, as well as calling prescribed emergency numbers such as the closest police station. In addition, to prevent secondary disaster, it is preferable to catch the immediate attention of anyone in the surrounding area to the occurrence of accident.

In the first exemplary embodiment, the external communicator 3 notifies prescribed addresses, and at the same time the accident alarm 4 notifies nearby vehicles and pedestrians of the occurrence of some breakdown or accident. More specifically, a red lamp and reflector are mounted in advance on the inside surface of the trunk hatch. If an accident occurs, drivers in cars behind are notified of a problem by the opening of the trunk, and turning on the red lamp. There are still other ways as described later.

As described above, the emergency equipment in the first exemplary embodiment of the present invention is equipped with the vehicle location estimator, accident detector such as a sensor, external communicator such as a mobile phone, and accident alarm for the surrounding area such as a hazard lamp. This enables the notification of prescribed addresses and immediately alerts drivers in surrounding vehicles and pedestrians. As a result, the victim of the accident may be rescued promptly.

Second exemplary embodiment

Figure 2:
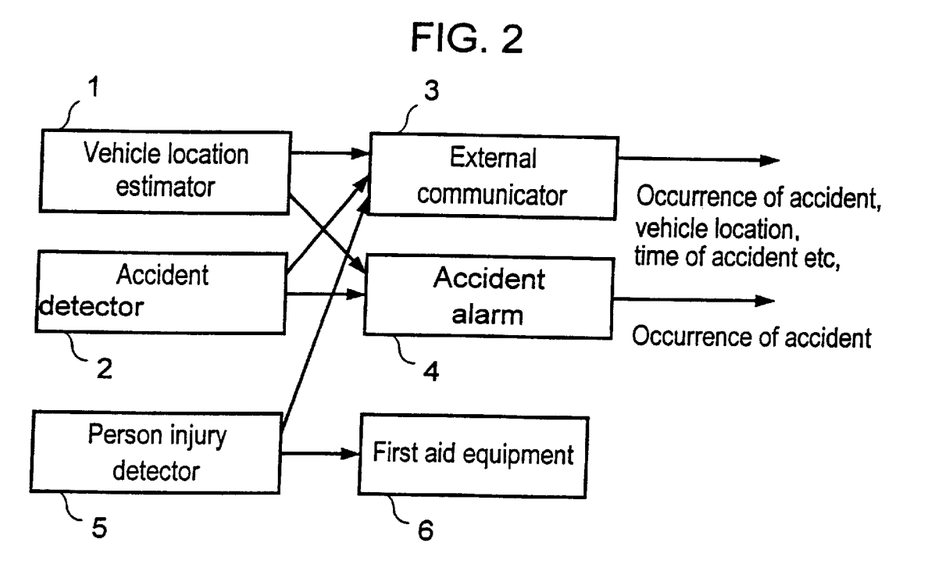
FIG. 2 is a block diagram of emergency equipment for use in the case of automobile accidents in accordance with a second exemplary embodiment in the present invention.

FIG. 2 is a block diagram of an emergency equipment for use in the case of automobile accidents in a second exemplary embodiment of the present invention. The second exemplary embodiment of the present invention comprises the vehicle location estimator 1 such as a GPS, accident detector 2 such as a sensor, external communicator 3 such as a mobile phone, accident alarm 4 such as a hazard lamp, an person injury detector 5, and first-aid equipment 6.

Since the operation of the vehicle location estimator 1, accident detector 2, external communicator 3, and accident alarm 4 have been discussed, their description is omitted here.

When the accident detector 2 detects the occurrence of an accident, the person injury detector 5 collects the health check data of the person in order to confirm the safety of the person. The health check data may include blood pressure, pulse, body temperature, dilation of pupils, and physical injury. More specifically, blood pressure, pulse, and body temperature after the accident may be measured by insertion of the finger into a tube sensor already installed in the car. Physical injury may be confirmed by installing a camera on board to visually identify a person's condition.

The first-aid equipment 6 may apply measures to prolong life of an injured person based on the information collected by the person injury detector 5. For example, the first-aid equipment 6 may increase the temperature inside the car if it determines that the person is in danger as a result of a drop in body temperature. Other forms of first-aid may include automated providing of an oxygen inhalator or a styptic.

The person's health check data obtained by the person injury detector 5 is also sent to a fire station and ambulance on its way to the accident site, through the external communicator 3. This will enable identification of the degree of damage and preparation of appropriate remedies.

As described above, the second exemplary embodiment comprises the vehicle location estimator, accident detector, external communicator, accident alarm for the surrounding area, person injury detector, and first-aid equipment. This configuration provides for attracting the attention of emergency parties and vehicles and pedestrians surrounding the accident site. Furthermore, active life-prolonging measures may be applied after confirming the injury suffered by the persons while requesting rescue of an injured person. This enables the increasing of the survival rate of any injured persons.

Third exemplary embodiment

Figure 3A:
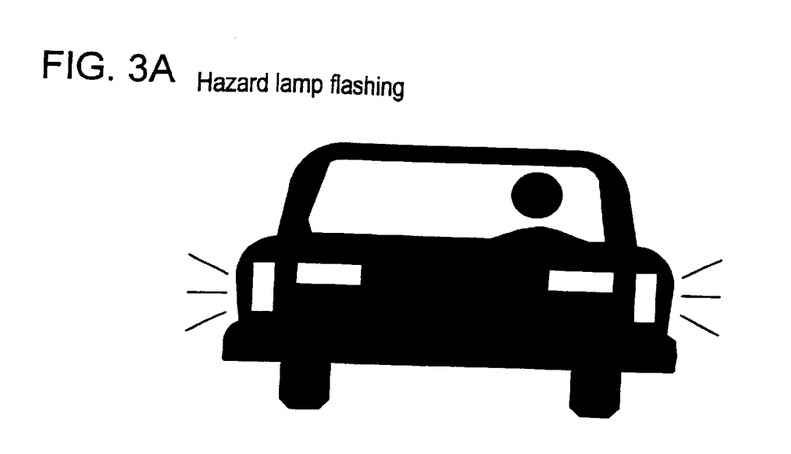
FIGS. 3(a) to 3(c) illustrate an accident alarm for the surrounding area of an emergency equipment for use in the case of automobile accidents in accordance with a third exemplary embodiment in the present invention.
Figure 3B:
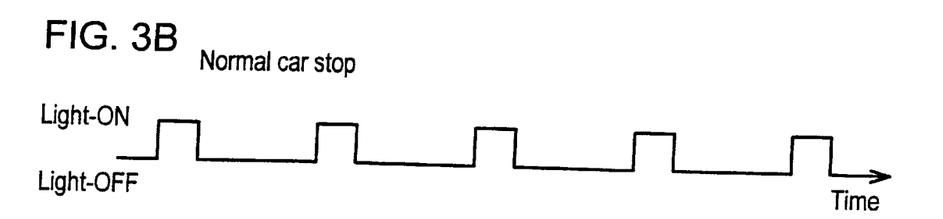
Figure 3C:
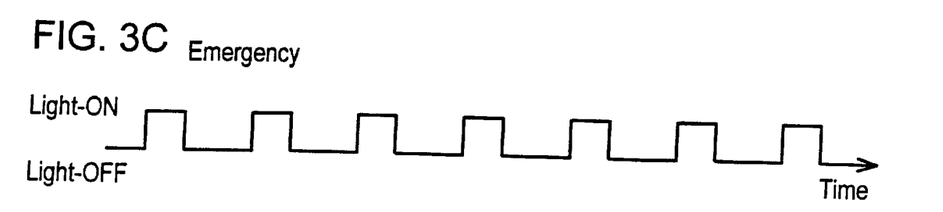

FIGS. 3(a) to (c) show the accident alarm for the surrounding area 4 employed in an emergency equipment for use in the case of automobile accidents in a third exemplary embodiment of the present invention.

In the third exemplary embodiment, hazard lamps are flashed at a rate faster than the normal flashing cycle.

FIG. 3(a) illustrates the lighting of the hazard lamps as the accident alarm 4 in the third exemplary embodiment of the present invention. FIG. 3(b) is a timing chart for turning on the hazard lamps when the hazard lamps are used in non-emergency situations such as when the car stops. The x-axis represents elapse of time for turning on the hazard lamps. FIG. 3(c) is a timing chart for turning on the hazard lamps when the accident alarm for the surrounding area 4 is activated by the occurrence of an accident.

As shown in FIG. 3(a), the accident alarm 4 of the emergency equipment in the third exemplary embodiment notifies surrounding vehicles and pedestrians of an emergency situation due to the occurrence of an accident by flashing the hazard lamps. However, a driver may flash the hazard lamps during normal parking. If the flashing condition is identical, people will not be able to differentiate between emergency and non-emergency situations. Accordingly, the accident alarm in the third exemplary embodiment flashes the hazard lamps in a faster cycle than normal flashing in emergency situations, as shown in FIG. 3(c), in order to inform surrounding vehicles and pedestrians of emergency due to an accident.

As described above, in the third exemplary embodiment, the accident alarm for the surrounding area 4 flashes the hazard lamps in a faster cycle than normal flashing so that people in the vicinity are notified immediately of a vehicle in a trouble due to an accident or other problems without regarding the sign as of no importance.

Fourth exemplary embodiment

Figure 4A:
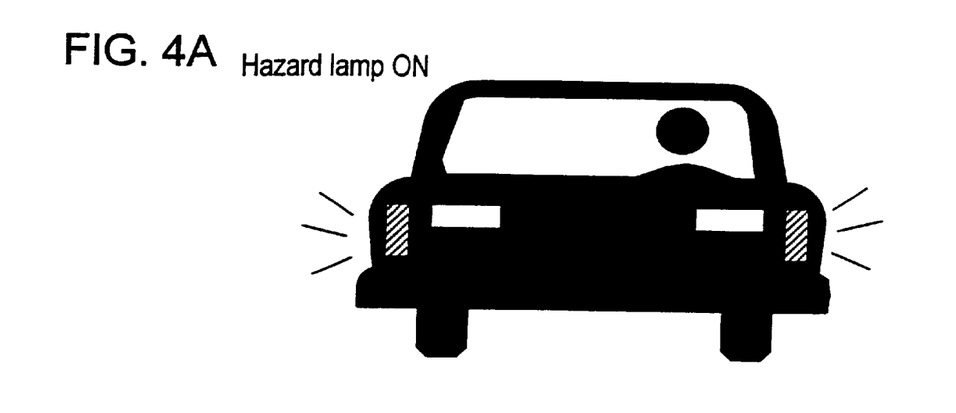
FIGS. 4(a) and 4(b) illustrate an accident alarm for the surrounding area of an emergency equipment for use in the case of automobile accidents in accordance with a fourth exemplary embodiment in the present invention.
Figure 4B:
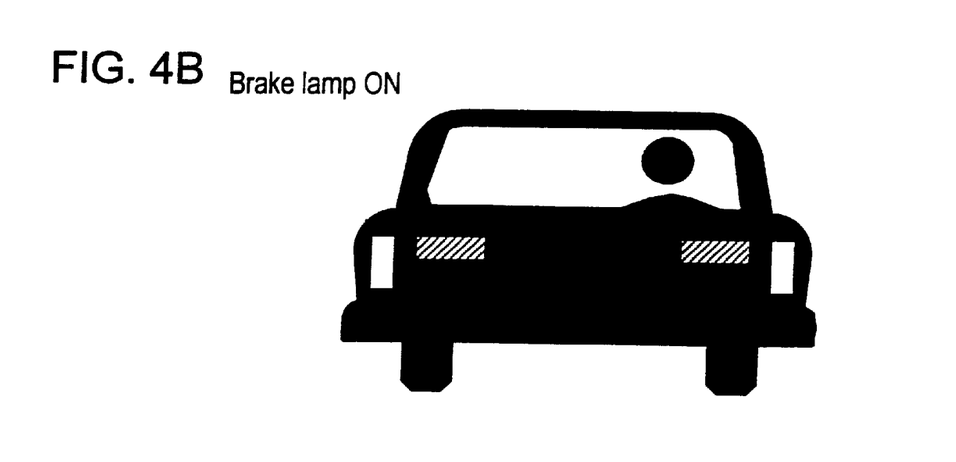

FIGS. 4(a) and 4(b) show the accident alarm for the surrounding area 4 employed in an emergency equipment for use in the case of automobile accidents in a fourth exemplary embodiment of the present invention.

In the fourth exemplary embodiment of the present invention, the emergency equipment for use in the case of automobile accidents turns on the hazard lamps and brake lamps alternately or the hazard lamps and head lamps alternately. FIG. 4(a) illustrates the case of turning on the hazard lamps as the accident alarm 4 in the fourth exemplary embodiment. FIG. 4(b) illustrates the case of turning on the brake lamps according to other timings as the operation of the same accident alarm 4.

The accident alarm 4 of the emergency equipment in the fourth exemplary embodiment notifies particularly the cars and pedestrians behind the automobile accident or other problem by alternately flashing the hazard lamps and brake lamps. Under normal conditions, this type of flashing never occurs. Accordingly, surrounding vehicles and pedestrians will immediately be alerted to the abnormal situation.

The fourth exemplary embodiment describes the case of using the brake lamps. By the use of the head lamps and hazard lamp, the same information may be notified to those in front of the vehicle involved.

As described above, in the fourth exemplary embodiment, the accident alarm for the surrounding area 4 alternately turns on the hazard lamps and brake lamps, or the hazard lamps and head lamps in order to ensure that the surrounding people is notified immediately of a vehicle in a trouble due to an accident or other problems without regarding the sign as of no importance.

Fifth exemplary embodiment

The accident alarm for the surrounding area 4 employed in an emergency equipment for use in the case of automobile accidents in a fifth exemplary embodiment of the present invention alternately turns on and off left and right hazard lamps, brake lamps, or head lamps mounted on both sides of the car so as to inform surrounding vehicles and pedestrians of an emergency due to an accident. Since this phenomenon never occurs under normal conditions, this 'winking,' if a pair of lamps are compared to human eyes, catches the attention of the surrounding people. Moreover, if the smog lamps are employed instead of the head lamps, attention may be attracted even under low visibility conditions such as in fog.

As described above, the fifth exemplary embodiment of the present invention alternately turns on and off the hazard lamps or brake lamps on the left and right. The blinking combination which never occurs under normal conditions enables to notify the surrounding people of the accident or problem of the car involved.

Sixth exemplary embodiment

The accident alarm for the surrounding area 4 employed in an emergency equipment for use in the case of automobile accidents in a sixth exemplary embodiment is a small broadcasting equipment for locally transmitting radio waves around an accident site. For example, the occurrence of an accident is automatically broadcast on a mini FM broadcasting station around the accident site. By transmitting information on a normal multiplex broadcast such as a FM multiplex broadcast, emergency information may be broadcast without interfering with normal programming. Naturally, this emergency information is ineffective unless nearby receivers are tuned to this particular frequency.

Another way is to receive always an applicable frequency using equipment on the road, which identify an accident site and time when receiving an emergency broadcast, and notify it to nearby vehicles and pedestrians.

As described above, the sixth exemplary embodiment employs a small radio transmitter for broadcasting accident information including the accident location and time of occurrence to unspecified people nearby. This enables the informing of surrounding vehicles and residents who cannot directly look at the site of the accident or any problem, i.e., not in a normal state, and catch their attention to ask for help.

Seventh exemplary embodiment

Figure 5:
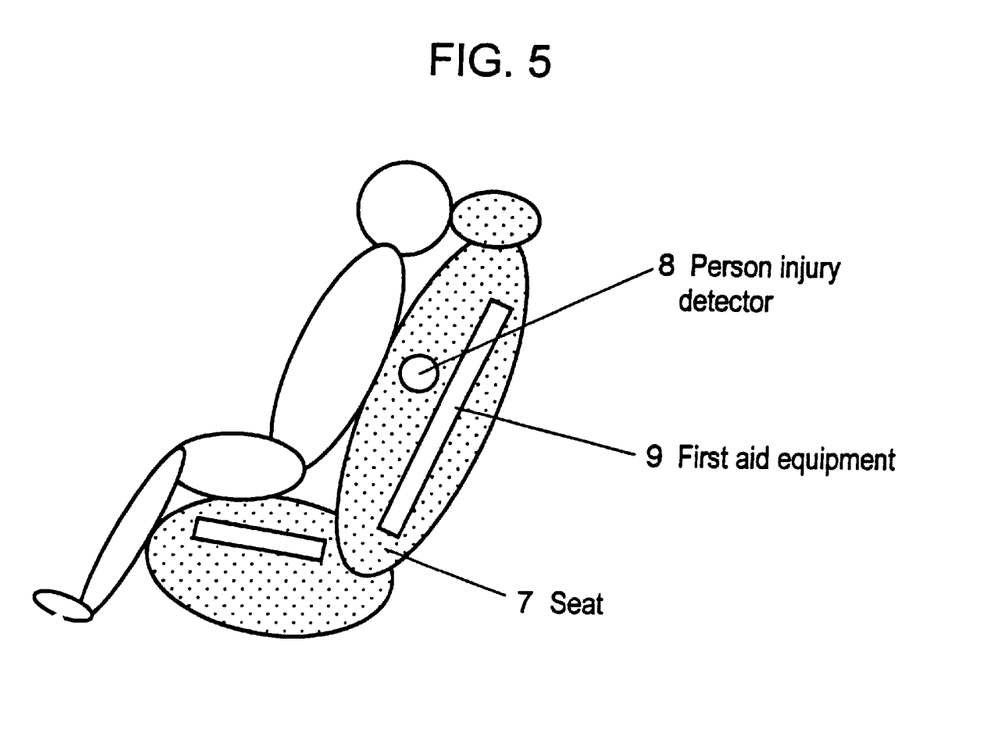
FIG. 5 is an person injury detector of an emergency equipment for use in the case of automobile accidents in accordance with a seventh exemplary embodiment, and a first-aid equipment of an emergency equipment for use in the case of automobile accidents in accordance with an eighth exemplary embodiment.

FIG. 5 illustrates a person injury detector 8 and first-aid equipment 9 employed in an emergency equipment for use in the case of automobile accidents in a seventh exemplary embodiment of the present invention.

In the seventh exemplary embodiment of the present invention, a detector embedded in the person's seat measures the person's body temperature, blood pressure, or pulse so as to recognize the condition of the person from any changes in body temperature, blood pressure, or pulse.

In FIG. 5, the person injury detector 8 employed in the emergency equipment in the seventh exemplary embodiment measures the person's body temperature, blood pressure, or pulse with the detector embedded in a seat 7 of the person. For example, body temperature may be measured with a thermometer. Pulse may be measured by detecting and counting minute vibration changes in the blood flow in the back contacting the seat 7. Blood pressure may also be estimated from the amplitude of the minute vibration changes. (It may also be measured from the change relative to that in the normal state.)

The condition of the person is identifiable from the changes in detected body temperature, blood pressure, or pulse. For example, as a person weakens, body temperature, blood pressure, and pulse decreases. Accordingly, it may be determined whether the person is still strong, slightly weakened, or in critical condition.

As described above, in the seventh exemplary embodiment, the detector embedded in the person's seat measures the person's body temperature, blood pressure, or pulse for recognizing the person's condition from changes in body temperature, blood pressure, or pulse. This makes it possible to obtain a range of data related to the person's condition simply by having the person contacting the seat without requiring any specific operation of the person.

Eighth exemplary embodiment

An emergency equipment for use in the case of automobile accidents in an eighth exemplary embodiment of the present invention activates a heater embedded in the seat of the person in response to recognition of damage to the person based on drop in body temperature, blood pressure, or pulse detected by the person injury detector 8.

As shown in FIG. 5, when the person injury detector 8 detects injury to the person based on drop in body temperature, blood pressure, or pulse and sends such information to the first-aid equipment 9, the first-aid equipment 9 employed in the emergency equipment in the eighth exemplary embodiment activates the heater embedded in the persons' seat to warm the person from the back so as to suppress any drop in body temperature. The entire car interior could be warmed; however, the engine often stops after the accident, and to turn on the engine when it is severely damaged may be dangerous. The heater therefore needs to be operated using the car battery or an emergency auxiliary battery. Accordingly, the heating of the person locally would be more effective than warming of the entire car interior.

As described above, in the eighth exemplary embodiment, the heater embedded under the person's seat is turned on in response to recognition of injury to the person based on drop in body temperature, blood pressure, or pulse detected by the person injury detector 8. This delays weakening caused by lowering body temperature of the injured person in danger of death, and prolongs life by maintaining physical strength as much as possible.

Ninth exemplary embodiment

Figure 6:
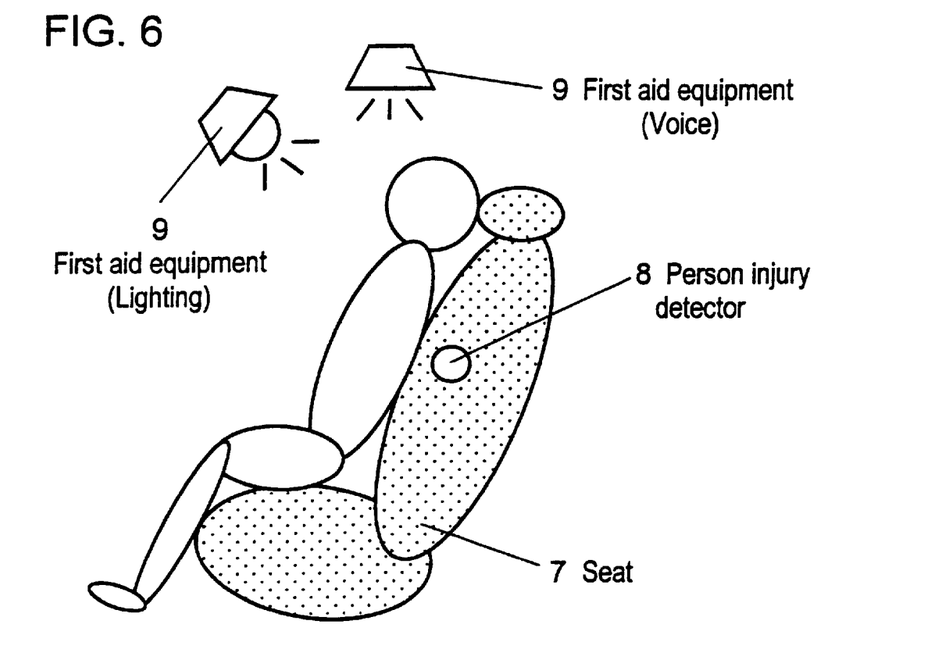
FIG. 6 is first-aid equipment of emergency equipment for use in the case of automobile accidents in accordance with a ninth exemplary embodiment.

FIG. 6 is the first-aid equipment 9 employed in an emergency equipment for use in the case of automobile accidents in a ninth exemplary embodiment of the present invention.

The emergency equipment in the ninth exemplary embodiment helps awaken the consciousness of the person through voice encouragement or a blinking light in response to the recognition of damage to the person based on drop in body temperature, blood pressure, or pulse.

There are two first-aid equipments in FIG. 6. One uses voice and the other uses light for restoring the person's consciousness.

As shown in FIG. 6, when the person injury detector 8 detects injury to the person indicated by drop in body temperature, blood pressure, or pulse, the first-aid equipment 9 tries to bring back the fainting person to full consciousness by means of a blinking light, or pre-recorded or synthesized voice encouragement such as "Stay awake!", or informing of the progress by using a message such as "The emergency center has been contacted. They'll be here in a short time" to psychologically encourage the person.

As described above, the ninth exemplary embodiment of the present invention aims to restore the consciousness of the person by voice encouragement or a blinking light in response to the recognition of damage to the person based on drop in body temperature, blood pressure, or pulse, in order to keep full consciousness of the injured person in danger of death, and encourage the person as much as possible to prolong life.

Tenth exemplary embodiment

Figure 7:
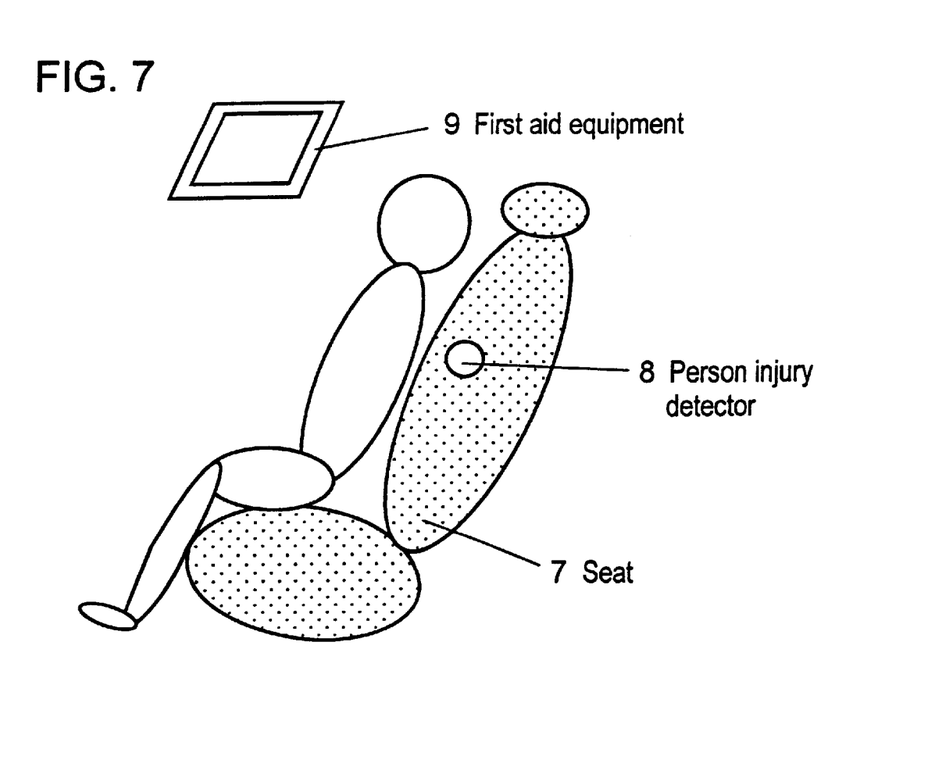
FIG. 7 is first-aid equipment of emergency equipment for use in the case of automobile accidents in accordance with a tenth exemplary embodiment.

FIG. 7 shows the first-aid equipment 9 employed in an emergency equipment for use in the case of automobile accidents in a tenth exemplary embodiment of the present invention.

The first-aid equipment 9 in the tenth exemplary embodiment explains the first-aid procedures by voice and images to the person.

In FIG. 7, the first-aid equipment 9 employed in the emergency equipment in this exemplary embodiment is equipped with a display (image display monitor) typically installed in a position so as to be easily seen by the person. When the person injury detector 8 determines that the person is injured, the first-aid procedures are explained by voice and picture images. For example, "If you are bleeding badly from an arm or leg, use the bandage in the glove box to tightly bandage the area a little away from the injured part closer to the heart.", and "Conserve your physical strength by reclining your seat and resting." Such contents are instructed by the voice, and an example picture image is shown on the display.

As described above, the tenth exemplary embodiment explains the first-aid procedures to the person by voice and picture images. This calms down the person even if a person is in a state of panic due to the sudden accident and resultant injury, allowing first-aid treatment to be promptly self-administered.

Eleventh exemplary embodiment

An emergency equipment in an eleventh exemplary embodiment of the present invention gives first-aid treatment to a person in response to the information on injury received from the person, instructions for refuge and guide, or instructions on emergency measures in response to recognition of the conditions of the damaged car and the surrounding area.

The first-aid equipment 9 employed in the emergency equipment in the eleventh exemplary embodiment detects the conditions of the damaged car and the surrounding area and gives instructions for refuge, guidance, or emergency measures, as well as giving first-aid treatment to the person, based on information received on the degree of injury to the person.

For example, if a gasoline leak is detected, a fire may break out triggered by some kind of spark in the car. In this case, the first-aid equipment 9 in the eleventh exemplary embodiment tells the person to immediately leave the car or instructs the person to set up a triangle indicator to prevent a secondary disaster.

As described above, the emergency equipment in the eleventh exemplary embodiment receives information on the condition of the person to allow the person to be given first-aid treatment, and also detects the condition of the damaged car and surrounding area to give instructions for refuge, guidance, and emergency measures in order to give first-aid in a broader sense including refuge and emergency measures.

Twelfth exemplary embodiment

An emergency equipment for use in the case of automobile accidents in a twelfth exemplary embodiment determines whether the present position of the car involved is on ordinary road or freeway based on information from the car navigation system, and gives instructions to the person on emergency measures suitable for each type of road.

The first-aid equipment 9 employed in the emergency equipment in the twelfth exemplary embodiment further determines whether the present position of the car is on an ordinary road or freeway based on an information from the car navigation system so as to give instructions to the person on emergency measures suitable for each type of road, in addition to the operation of the first-aid equipment 9 in the eleventh exemplary embodiment. For example, if the car is on a freeway, it is dangerous to get out of the driver's seat. Accordingly, the first-aid equipment 9 gives instructions not to get out of the car unless necessary, or to carefully get out from the passenger's seat, and gives the emergency addresses to inform of the accident.

As described above, the emergency equipment in the twelfth exemplary embodiment determines whether the car is on ordinary road or freeway based on the information from the car navigation system, and informs the person of emergency measures suitable for each type of road.

This enables the application of more appropriate emergency instructions in accordance with the characteristics of each type of road and the degree of danger.

Thirteenth exemplary embodiment

The person injury detector 8 employed in an emergency equipment for use in the case of automobile accidents in a thirteenth exemplary embodiment of the present invention is equipped with a conversation equipment or interactive information input equipment, in addition to the operation of the person injury detector 8 in the seventh exemplary embodiment. It is also for communicating with the person in order to receive information from the person as well as receiving information from the person injury detector 8.

Even though conditions such as the blood pressure of the person may be detected by the sensor embedded in the seat, as in the person injury detector 8 in the seventh exemplary embodiment, it is often difficult to identify the cause of injury, present condition including pain, and which senses are active. Accordingly, when the person is conscious, information may be obtained by communicating with the person, and the present conditions and degree of injury are recognizable based on such information. For example, "Do you have any pain anywhere?," "Where is it hurting?," "Are you bleeding?," and "Can you move?" are asked, and the person may answer verbally or by pressing a yes/no button.

The first-aid equipment 9 can give appropriate first-aid instructions to the person based on further detailed information from the person injury detector 8. For example, the first-aid equipment 9 automatically warms the seat, and also gives instructions on how to stop bleeding or splint broken bones depending on the situation. Naturally, the first-aid equipment 9 psychologically encourages the person by telling him or her that a rescue squad is on the way.

As described above, the thirteenth exemplary embodiment receives information by communicating with the person, and gives appropriate first-aid instructions to the person based on the injury recognition result. By obtaining information directly from the person after calming them if they are upset due to the sudden accident, or by making the person treat themselves, appropriate first-aid treatment may be given promptly.

Fourteenth exemplary embodiment

The accident alarm for the surrounding area 4 of an emergency equipment in a fourteenth exemplary embodiment of the present invention automatically beeps a horn intermittently for a long time to notify any surrounding vehicles or pedestrians of the emergency situation caused by the accident.

For example, the accident alarm for the surrounding area 4 honks the horn on and off regularly for one minute, remains silent for the next minute, and then honks the horn on and off regularly for one minute again. A complete off period is included in order to use the battery efficiently, which is a limited energy source.

As described above, in the fourteenth exemplary embodiment, the horn is automatically honked intermittently for long time so that the surrounding people is immediately informed of the car in the accident or trouble by hearing continuous horn sound which normally does not happen.

Fifteenth exemplary embodiment

The accident alarm for the surrounding area 4 of an emergency equipment for use in the case of automobile accidents in a fifteenth exemplary embodiment of the present invention immediately honks the horn when it receives signals from an approaching emergency vehicle such as an ambulance, in addition to the operation of the accident alarm for the surrounding area 4 in the fourteenth exemplary embodiment. If the accident occurs in an area with a restricted view, or in a difficult place to find, the ambulance may not be able to reach the car even it is within short distance. Therefore, even when the horn is turned off for energy-saving reasons, the accident alarm for the surrounding area 4 turns on the horn immediately after receiving signals from the approaching ambulance so that the accident location is identifiable.

As described above, the fifteenth exemplary embodiment of the present invention automatically sounds the horn even when receiving signals from the emergency vehicle such as an ambulance so that emergency vehicles such as an ambulance can find the car involved sooner, reducing the time taken for rescue.

What is claimed is:

1. An emergency assistance system for vehicular accidents, comprising:
    a vehicle location estimation means for estimating position of a vehicle;
    an accident detection means for detecting the occurrence of an accident
    an external communication means for notifying an emergency response organization of accident related information;
    an accident alarm means for announcing the occurrence of an accident within the vicinity of an accident site;
    an injured person detection means for detecting if a person has been injured; and
    first-aid means for use in providing first-aid treatment to an injured person based on detection by said injured person detector.

2. The emergency assistance system as defined in claim 1, wherein said accident alarm means is one of:
    flashing hazard lamp;
    alternately flashing hazard lamp and brake lamps;
    alternately flashing hazard lamp and head lamps; and
    alternately flashing left and right lamps of one of i) hazard lamps and ii) brake lamps.

3. The emergency assistance system as defined in claim 1, wherein said accident alarm means is a radio transmitter for communicating with unspecified persons near the accident site.

4. The emergency assistance system as defined in claim 1, wherein said injured person detection means measures one of the person's body temperature, blood pressure, and pulse using a detector embedded in the person's seat.

5. The emergency assistance system as defined in claim 1, wherein said first-aid means activates a heater embedded in a seat.

6. The emergency assistance system as defined in claim 1, wherein said first-aid means is for use in restoring consciousness of an injured person by one of voice communication and a blinking light.

7. The emergency assistance system as defined in claim 1, wherein said first-aid means provides first-aid procedures by one of voice instructions and picture images.

8. The emergency assistance system as defined in claim 1, wherein said first-aid means provides for first-aid treatment to the injured person in response to information on the degree of injury of the person.

9. The emergency assistance system as defined in claim 8, wherein said first-aid means determines the type of road where the vehicle is located.

10. The emergency assistance system as defined in claim 1, wherein said injured person detection means receives information from the injured person using one of:
    i) voice communication means, and
    ii) interactive information input means;
    and said first-aid means gives first-aid instructions to the injured person in response to the results detected by said injured person detection means.

11. The emergency assistance system as defined in claims 1, wherein said accident alarm means provides for activating a horn automatically and intermittently.

12. The emergency assistance system as defined in claim 11, wherein said accident alarm means automatically activates a horn when receiving signals from an emergency vehicle approaching the accident site.

13. The emergency assistance system as defined by claim 8, wherein said first-aid means also provides instructions for emergency measures in response to a recognition of the condition of the vehicle.

14. The emergency assistance system as defined by claim 2, wherein said hazard lamp is flashed at a high cycle rate.

15. The emergency assistance system as defined by claim 1, wherein the results detected by said injured person detection means is communicated to an emergency response organization by said external communications means.

16. The emergency assistance system as defined by claim 1, wherein said injured person detection means detects the degree of injury of a person.

17. The emergency assistance system as defined by claim 1, wherein said injured person detection means detects change in vital signs of a person.

18. The emergency assistance system as defined by claim 1, wherein the accident related information includes at least one of accident vehicle location, driver's condition and type of accident.

19. The emergency assistance system as defined by claim 1, wherein said accident detection means detects the occurrence of an accident by one of manual operation means and an onboard sensor.

* * * * *